(12) United States Patent
Fleischmann

(10) Patent No.: US 6,557,487 B1
(45) Date of Patent: May 6, 2003

(54) METHOD AND DEVICE FOR REARING INSECTS, ESPECIALLY FOR OBTAINING A SECRETION FROM FLY LARVAE FOR THERAPEUTIC APPLICATION

(76) Inventor: Wilhelm Fleischmann, Wieselweg 26, 74321 Bietigheim-Bissingen (DE)

( * ) Notice: Subject to any disclaimer, the term of this patent is extended or adjusted under 35 U.S.C. 154(b) by 0 days.

(21) Appl. No.: 09/762,575

(22) PCT Filed: Jun. 6, 2000

(86) PCT No.: PCT/EP00/05132

§ 371 (c)(1),
(2), (4) Date: Feb. 8, 2001

(87) PCT Pub. No.: WO00/74478

PCT Pub. Date: Dec. 14, 2000

(30) Foreign Application Priority Data

Jun. 8, 1999 (DE) ............................... 199 25 996

(51) Int. Cl.[7] ............................................... A01K 29/00
(52) U.S. Cl. .......................................... 119/6.5
(58) Field of Search .................... 119/6.5, 6.6

(56) References Cited

U.S. PATENT DOCUMENTS

| 3,468,289 A | * | 9/1969 | Broida | 119/496 |
|---|---|---|---|---|
| 4,417,545 A | * | 11/1983 | Finney | 119/6.6 |
| 4,646,683 A | * | 3/1987 | Maedgen, Jr. | 119/6.5 |
| 4,765,275 A | * | 8/1988 | Yukawa et al. | 119/6.5 |
| 4,785,764 A | * | 11/1988 | Muller | 119/416 |
| 5,074,247 A | * | 12/1991 | Gupta et al. | 119/452 |
| 5,351,643 A | * | 10/1994 | Hughes | 119/6.5 |
| RE35,348 E | * | 10/1996 | Georgi | 119/6.6 |
| 5,784,991 A | * | 7/1998 | Ukishiro et al. | 119/6.5 |
| 5,927,230 A | * | 7/1999 | Frank et al. | 119/6.5 |
| 6,359,189 B1 | * | 3/2002 | Fleischmann | 602/41 |

FOREIGN PATENT DOCUMENTS

| WO | WO 92/11760 | * | 7/1992 | ........... A01N/1/02 |
| WO | WO 95/26633 | * | 10/1995 | .......... A01N/59/04 |

OTHER PUBLICATIONS

S Thomas B Pharm., PhD., Maggots in Wound Debridement—an Introduction, Mar. 22, 1999.*

* cited by examiner

Primary Examiner—Charles T. Jordan
Assistant Examiner—Kimberly S. Smith
(74) Attorney, Agent, or Firm—Pendorf & Cutliff

(57) ABSTRACT

The invention relates to the rearing of insects, especially for the therapeutic application of the secretion of fly larvae (maggots). The eggs of the flies are stored and/or transported in a container under conditions that inhibit their development. For application, the eggs are removed from the development-inhibiting conditions and placed under conditions in which they can be reared and fed so that the maggots hatch out, grow and secrete the secretion to be applied.

6 Claims, No Drawings

METHOD AND DEVICE FOR REARING INSECTS, ESPECIALLY FOR OBTAINING A SECRETION FROM FLY LARVAE FOR THERAPEUTIC APPLICATION

BACKGROUND OF THE INVENTION

1. Field of the Invention

Process and device for rearing of insects, in particular for obtaining the secretions of fly larvae for therapeutic application.

The invention concerns a process and a device for rearing insects, in particular for obtaining the secretions of fly larvae (maggots) for therapeutic application.

2. Description of the Related Art

For treatment of wound infections and wounds, which contain necrotized tissue, for example for treatment of diabetic gangrene, fly larvae, so-called maggots, are employed, in particular larvae of Diptera from the family Muscidae, Sarcophaginae and Calliphoridae (for example, Lucilia, Blue Bottle). The larvae are introduced for a certain amount of time, for example, approximately three days, into a wound for which it is difficult to render therapy. It has been shown that the larvae within this time removed necrotized tissue in the wound, eliminated bacterial infections, and stimulated wound healing. This effect is in particular brought about by the digestive secretions excreted by the maggots. This secretion fluidizes the necrotized tissue, so that it can be ingested by the maggots as nutrition. The secretion further has a strongly bactericidal effect and promotes wound healing.

In this method of treatment it is necessary to have living maggots available which can be applied to the wound so that they secrete the healing secretions. This brings about, for the employment of this method, a substantial logistical problem, since the period of time of the active maggot stage, in which the healing secretions are secreted, is relatively short and has a duration of only a few days. It is necessary that the maggots be transported from the producer, who breeds the maggots, to the user immediately prior to application. This necessitates an exactly coordinated plan. Besides this, the maggots are relatively sensitive and must be provided with air and nutrients during transport. On the basis of these difficulties, the employment of the fly larvae therapy is limited in its possibilities and full advantage cannot be taken thereof.

SUMMARY OF THE INVENTION

The invention is based on the task of providing a process and a device through which the breeding of insects can occur in a controlled manner, and in particular, through which the therapeutic application of fly larvae secretion is simplified and facilitated.

DETAILED DESCRIPTION OF THE INVENTION

The essential idea of the invention is comprised therein, that the breeding of the insects is to be carried out in an enclosed biotope under exactly defined environmental conditions, as a result of which the development cycle can be intentionally influenced. Thereby it is made possible to study the development and the behavior of the insects under targeted, varied physical, chemical, biochemical, and biological conditions and to influence the conditions for the medical-therapeutic and pharmaceutical use. Thereby, the speed of the development cycle can be influenced by changing the conditions, that is, it can be delayed or accelerated. Besides this, it becomes possible by targeted, influenced measures to raise the quality and the yield.

In the utilization of the process for obtaining the secretion of fly larvae for therapeutic application, one essential aspect is comprised in arresting the development of the fly larvae in the egg stage and to store and/or to transport these eggs under development retarding conditions. At the manufacturer, who breeds the flies, the fly eggs are separated and preferably disinfected so that they are sufficiently sterile. The sterilized eggs are enclosed in a self-enclosed biotope, for example a container, in which the further development of the eggs is carried out or maintained under restrictive or retarding conditions. Such conditions could include that the eggs are cooled and/or stored in a dehumidified atmosphere. Further, the eggs can be stored in an oxygen-poor atmosphere, in which the container is, for example, evacuated or filled with an inert gas. Further possible are reversible chemical/biochemical influences (for example Neb-TMOF), which results in oostasis for a defined period of time. These measures can be employed individually or in combination. These resilient and tolerant eggs can be kept alive for prolonged periods of time under these restrictive development conditions. This makes it possible for the producer to store the eggs for a certain period of time. Further, the eggs can be transported to the user in simple manner under these conditions, without risk of damage. It is further possible for the end user to maintain a certain supply of eggs, for example in a clinic, for a certain period of time, so that the respective actual needs can be satisfied.

If the maggot secretion is to be applied, then the user reactivates the further development of the eggs into the larval stage. For this, the development retarding conditions are lifted and the eggs are subjected to incubating conditions, so that they further develop and within a short period of time hatch into maggots. Since the eggs are sterilized at the producer, the hatched maggots are also sterile and can be employed without problem.

It is also possible to culture microorganisms in the artificially produced microbiologically-closed living environment, in order to heighten or to change the effect of the maggots and their microbiologically modified secretions.

The maggots can be introduced immediately into the wound in the known manner, and after a certain treatment time must again be removed from the wound. In one variation, the maggots are introduced in the wound in an application container. One such application container includes a fluid transmissive wall, which however does not allow passage of the maggots enclosed in the application container. For example, the application container can be a flexible bag with a net-like wall. The secretion secreted by the maggots can pass through the wall of the application container and into the wound. The wound tissue fluidized by the secretion can likewise pass through the wall of the application container and be taken up by the maggots. An application container of this type has the advantage, that the maggots and therewith the secretions secreted by these maggots can be applied in targeted, localized manner. Besides this, maggots can be removed from the wound in simple manner, together with the application container.

Finally, it is also possible to bring the maggots into contact with a porous wound insert, which absorbs the secretions secreted by the maggots. In this case, the wound insert soaked with the secretion is applied to the wound. This has the advantage, that the wound insert can be applied temporally and spatially separate from the maggots, which simplifies the application and avoids the problem of the occasional patient refusing treatment with living maggots.

Preferably the incubation of the eggs up to the hatching of the maggots occurs in an incubation container. The eggs are introduced in this incubation container and incubated at a temperature of between 20 and 40° C. The incubation container is provided with sufficient nutrient substances and air for the hatching larvae, so that these can develop up to the larval stage, at which they secrete the therapeutic secretions. This incubation container is preferably produced as a bag comprised of plastic foil and preferably includes an absorbent material for absorbing the produced active substances under sterile or microbiologically controlled conditions.

In a preferred embodiment, the eggs can be enclosed in an application container and introduced into the incubation container. These small eggs are kept in the application container by the incubation container, so that they do not fall out of this net-like wall. When the larvae hatch out of the eggs, they can take up the nutrient substances from out of the incubation container and grow in the application container to the size at which they secrete the therapeutically active secretions. At this size, they can no longer slip out of the net-like wall of the application container. The application container can then be removed from the incubation container, or as the case may be, the incubation container can be moved from the application container, so that the maggots can be applied to the wound directly with the application container, or can be brought into contact with a porous wound insert.

In an embodiment particularly simple for the user, the eggs are introduced into the incubation container already by the producer and initially maintained at development retarding conditions for storage and transport. For this, the incubation containers are evacuated, or filled with a dried inert gas, or are chemically/biochemically oostatically manipulated. Likewise, or in certain cases additionally, the incubation containers can be placed in a cooling container and cooled for storage and transport.

When the maggots are to be applied, incubation conditions are established in the incubation containers. For this, the incubation containers, together with the eggs, are introduced into a warm environment. The incubation containers are supplied with oxygen-containing air, the nutrients necessary for the hatching larvae, and in certain cases, activating chemical or biochemical factors (for example peptidases). For administration of oxygen, the wall of the incubation container can be punctured with a canula, or an opening can be provided. As appropriate, it is also possible to introduce the necessary nutrients and, in certain cases, to introduce the oostatic influencing deactivating substances into the incubation container in this manner. In a variation particularly convenient for the user, it is possible that air, nutrient solutions, and other substances are provided in the incubation container during the manufacture thereof in enclosed containers or enclosed ampullae's, which can be disrupted by the user, so that air and nutrient solutions, as well as in certain cases chemical, biochemical, and microbiological components, are released into the incubation containers, which promotes hatching and which can be taken up by the hatched maggots.

If the flies are transported to the user in the egg stage, so that the maggots are hatched by the user for the application of the secretion, then as a rule, the maggots are terminated as soon as they are removed from the wound, or after they have secreted the secretion onto the wound insert.

At the producer, preferably utilizing a component of the population of the insects, the complete development cycle is carried out in a time-wise modifiable and controllable biotope. After the hatching of the maggots, these are in certain cases used for obtaining the secretion, which then is made available for the user in the a form suitable for application, or for manufacture of pharmaceutical preparations. At the end of the larvae stage, the conditions necessary for pupating are then established in the biotope, for example drying air conditions. The maggots then pupate so that a new generation of insects hatches, which can then again be used for depositing of eggs under sterile conditions. The raising of the insects from egg up to hatched fly under time-wise, manipulable and controllable conditions provides the producer with the possibility to match the time and yield of the production of the maggots, or as the case may be, the maggot secretions, to the market requirements. Besides this, the insect populations can be bred and influenced, in order to achieve an increase in productivity and quality. Finally, a targeted microbiological influence on the closed development biotope is possible, so that a therapeutic synergistic effect can be achieved, for example by the select supplementation of bacteria to the secretions secreted by the maggots.

What is claimed is:

1. A process for therapeutic application of secretions of fly larvae (maggots) on a wound, the method comprising the steps of:

providing an application container;

introducing fly eggs into the application container, maintaining the application container under conditions which retard the further development of the eggs for storage;

introducing the application container into an incubation container;

maintaining the eggs in controlled incubating conditions in the incubation container;

developing the fly larvae from the egg stage up to the maggot stage inside the application container, wherein development conditions are influenced in a controlled manner, wherein the maggots are grown until they secrete a therapeutically active secretion;

removing the application container from the incubation container;

applying the application container into the wound;

wherein the application container includes fluid transmissive walls that allows the passing of secretions produced by the maggot through the walls of the application container into the wound but prevents passage of the maggots enclosed in the application container.

2. The process according to claim 1, wherein the time period of the egg stage is controlled during at least one of storage and transport by establishment, maintenance, and removal of development retarding conditions in the application container.

3. The process according to claim 1, wherein the eggs are transported to a user under development-retarding conditions, and wherein before beginning the incubation conditions, the development retarding conditions are eliminated to allow the maggots to hatch and develop to the stage at which they secrete the therapeutically active secretions.

4. The process according to claim 1, wherein the eggs are sterilized eggs.

5. The process according to claim 2, wherein the conditions for retarding the further development of the eggs includes at least one of cooling, dehumidification, evacuation, an inert gas atmosphere, and chemical or biochemical retardants, individually or in combination.

6. The process according to claim 1, wherein an enclosed biotope is established and maintained surrounding the application container.

* * * * *